(12) United States Patent
Vignalou-Marche

(10) Patent No.: US 7,577,530 B2
(45) Date of Patent: Aug. 18, 2009

(54) METHOD OF ANALYZING INDUSTRIAL FOOD PRODUCTS, COSMETICS, AND/OR HYGIENE PRODUCTS, A MEASUREMENT INTERFACE FOR IMPLEMENTING THE METHOD, AND AN ELECTRONIC SYSTEM FOR IMPLEMENTING THE INTERFACE

(75) Inventor: Anne Vignalou-Marche, Palaiseau (FR)

(73) Assignee: Compagnie Gervais Danone (FR)

( * ) Notice: Subject to any disclaimer, the term of this patent is extended or adjusted under 35 U.S.C. 154(b) by 299 days.

(21) Appl. No.: 10/951,235

(22) Filed: Sep. 27, 2004

(65) Prior Publication Data

US 2006/0041386 A1 Feb. 23, 2006

(30) Foreign Application Priority Data

Aug. 20, 2004 (FR) .................................. 04 09033

(51) Int. Cl.
*G01N 33/48* (2006.01)
(52) U.S. Cl. ........................................................ 702/19
(58) Field of Classification Search .................... 702/19
See application file for complete search history.

(56) References Cited

U.S. PATENT DOCUMENTS 3,935,650 A 2/1976 Hully et al.

OTHER PUBLICATIONS

Guinard J-X et al., "Computerized Procedure for Time-Intensity Sensory Measurements", *Journal of Food Science, Institute of Food Technologists*, Chicago, Illinois, vol. 50, No. 2, 1985, pp. 543-546.
Bruine De Bruin et al., "Order effects in sequentially judged options due to the direction of comparison", *Organizational Behavior and Human Decision Processes*, Academic Press, vol. 92, No. 1-2, 2003, pp. 91-101.

Peleg et al., "Bitterness and astringency of flavan-3-ol monomers, dimmers and trimers", *Journal of the Science of Food and Agriculture, Elsevier Applied Science Publishers*, Great Britain, vol. 79, No. 8, 1999, pp. 1123-1128.
Vandali et al., "Speech Perception as a Function of Electrical Stimulation Rate: Using the Nucleus 24 Cochlear Implant System", *Ear and Hearing, Williams and Wilkins*, vol. 21, No. 6, Dec. 2000, pp. 608-624.
Martin et al., "Comparison of odour sensory profiles performed by two independent trained panels following the same descriptive analysis procedures", *Food Quality and Preference, Longman Scientific and Technical*, Great Britain, vol. 11, No. 6, 2000, pp. 487-495.

*Primary Examiner*—Jerry Lin
(74) *Attorney, Agent, or Firm*—Alston & Bird LLP

(57) ABSTRACT

The invention seeks to improve the taking of physical measurements on an industrial product represented by organoleptic perceptions, the method providing a measurement interface that submits descriptors in a relative arrangement such that testers are not influenced by the order in which they appear, regardless of the descriptor and regardless of the field of the descriptor. For this purpose, the invention provides a method of analyzing industrial products in order to characterize them, in order to distinguish between them, and/or in order to modify them so as to improve them, by analyzing the responses of a panel of testers in application of certain descriptors. The method comprises steps consisting in selecting descriptors that are a priori pertinent for determining the organoleptic characteristics of the products; selecting a response mode; providing all of the descriptors simultaneously to the panel of testers on a single occasion and for a determined duration in a measurement interface presenting a center and an input zone for each descriptor, the input zones being distributed uniformly over at least a section of at least one conic about the center of the interface; collecting the responses from each tester as a function of the selected response mode; recording the responses; and analyzing the responses using at least one statistical method.

16 Claims, 7 Drawing Sheets

METHOD OF ANALYZING INDUSTRIAL FOOD PRODUCTS, COSMETICS, AND/OR HYGIENE PRODUCTS, A MEASUREMENT INTERFACE FOR IMPLEMENTING THE METHOD, AND AN ELECTRONIC SYSTEM FOR IMPLEMENTING THE INTERFACE

The invention relates to a method of analyzing industrial products, to a measurement interface for implementing the method, and to an electronic system for implementing the interface.

BACKGROUND OF THE INVENTION

When manufacturing a food product, a cosmetic, and/or a hygiene product, numerous analyzes can be performed regularly in order to monitor the composition of the product and its state of hygiene (quality control, hazard analysis and critical control point (HACCP), etc.). These analyses are generally implemented by means of automatic machines capable of giving very precise quantitative results on said composition or hygiene states (quantity of bacteria, quantity of each element, etc.).

However, it is also appropriate to perform organoleptic analyses during creation of a product or while it is being renovated, i.e. when similar competing products are on the market and it is necessary to offer a product having its own "character", while nevertheless conserving the original qualities of the basic product.

These analyses are performed by panels of testers who are trained and selected for being representative of a population, for their ability to distinguish as objectively and as accurately as possible between different descriptors for the product (i.e. different aromas, different textures, intensities, etc.), and for giving responses that are accurate and objective.

In general, organoleptic analyses are performed under conditions which are strict in order to obtain responses that are free from any outside influence, for example:

it is known to perform wine tasting in glasses that are blue so that testers are not influenced by the color of the wine;
  tasting rooms are neutral in color and soundproof so that testers are not subjected to any outside influence;
  red lighting can be used to mask characteristic color;
  tasting stations are spaced apart from one another so that testers do not influence one another by their behavior; and
  the product samples are given in an order specific to each tester.

The responses to such qualitative analyses are then processed statistically in application of various relationships selected depending on the type of analysis.

The interpretation and the pertinence of such results depend on the qualities of the responses of the testers.

In general, in order to facilitate statistical analysis, a list of descriptors is given to each tester who is required to select from said list when describing perceptions and giving them marks corresponding to their intensities.

However, studies undertaken by the Applicant have shown that in spite of recommendations, testers generally mark descriptors, e.g. for intensity, in the order in which they are read successively from the list supplied to them, and not in the order in which a descriptor appears and/or becomes pertinent during tasting.

That method of proceeding presents major drawbacks:

Certain descriptors are poorly marked or not marked at all. For example, for a cake, the list of descriptors is as follows: chocolate, sweet, bitter, crunchy. Testers give their perceptions relative to those descriptors in the order they appear in the list. However, if a tester initially perceives bitterness followed by the taste of chocolate and then begins by marking the descriptor chocolate, because it is at the top of the list, the tester will give marks to the descriptor bitterness after a delay that is sufficient to falsify the result compared with that tester's real perception. The magnitude of this problem increases with increasing length of the list of descriptors given to testers.

When using dynamic study methods (methods which consist in measuring the sensations perceived over time while tasting a product; with time being taken into account in order to measure the dynamic behavior of the product and reveal how the sensations perceived vary while tasting is taking place), the expected results are falsified since with such methods the products are characterized not only by the intensities of the descriptors, but also and above all by the timing with which said descriptors appear. Thus, a tester wasting time in consulting the list to find the descriptor that has just been perceived, while continuing to perceive other descriptors, runs a critical risk of reversing the order in which said descriptors appear, and the marking is thus falsified.

OBJECTS AND SUMMARY OF THE INVENTION

The present invention seeks to eliminate this problem of influencing testers both in terms of perception and also in transcribing said perception so as to improve the physical measurements of an industrial product as represented by organoleptic perceptions.

To do this, the invention thus proposes providing a measurement interface that submits descriptors in a relative arrangement such that testers are not influenced by the order in which they appear, and regardless of the particular descriptor and of the field to which it relates (a descriptor relating to taste, texture, olfaction, feel, sight, hearing, touch, etc.).

More precisely, the invention provides a method of analyzing industrial food products, cosmetics, and/or hygiene products in order to characterize them, distinguish between them, and/or modify them in order to improve them, by analyzing the responses of a panel of testers to certain descriptors, said method comprising the steps consisting in:

a) selecting descriptors that are a priori pertinent for determining the organoleptic characteristics of the products;

b) selecting a response mode selected from the group constituted by an on/off binary mode, a continuous mode over a range of values, and a discrete mode over a range of values;

c) providing all of the descriptors simultaneously to the panel of testers for a determined duration in a measurement interface presenting a center and an input zone for each descriptor, the input zones being distributed uniformly over at least a section of at least one conic about the center of the interface;

d) collecting the responses from each tester as a function of the selected response mode;

e) recording the responses; and f) analyzing the responses using at least one statistical method.

The invention also provides a measurement interface for implementing the above method, which interface comprises a plurality of input zones, there being the same number of input zones as there are descriptors selected in step a) of the method, said input zones being distributed uniformly along at least a section of at least one conic about a center of the interface.

In another aspect, the invention provides an electronic system for implementing the above interface, which system:
- initiates a memory when tasting begins at time t0;
- times the tasting;
- records the time at which the response of each tester occurs;
- forms a multidimensional memory of cells having one dimension corresponding to the descriptors and one dimension corresponding to the testers, and in which each cell corresponds to the combination of one descriptor and one tester;
- stores in each cell at least one time at which the descriptor occurs for each tester, it being possible for an occurrence time to be null if the tester does not select the descriptor during tasting;
- performs statistical processing on the cells applying a method previously selected by the operator;
- stores the results of said processing in a memory; and
- provides a record of the results in a display of the organoleptic characteristics of the products as a function of time.

BRIEF DESCRIPTION OF THE DRAWINGS

Particular embodiments of the invention are defined in the secondary claims. Other characteristics of the invention appear in the following detailed description made with reference to the accompanying figures in which, respectively:

FIGS. 3a and 3b show an input zone in an on/off binary mode;

FIG. 4 shows an input zone in a mode that is continuous over a range of values;

FIGS. 5a and 5b show an input zone in a mode that is discrete over a range of values;

MORE DETAILED DESCRIPTION

In the description below, the descriptors are given by way of non-limiting indication, the invention not relating to providing defined descriptors in a given field, but to an interface suitable for receiving information in the form of data, independently of the nature of said information, and suitable for simplifying the inputting of data and for improving the accuracy of the input data in the context of an industrial method for analyzing and/or improving manufactured products.

The term "organoleptic" should be understood as characterizing the properties of a body in simulating any type of sense receptor (taste, smell, sight, hearing, feel).

Figure 1:
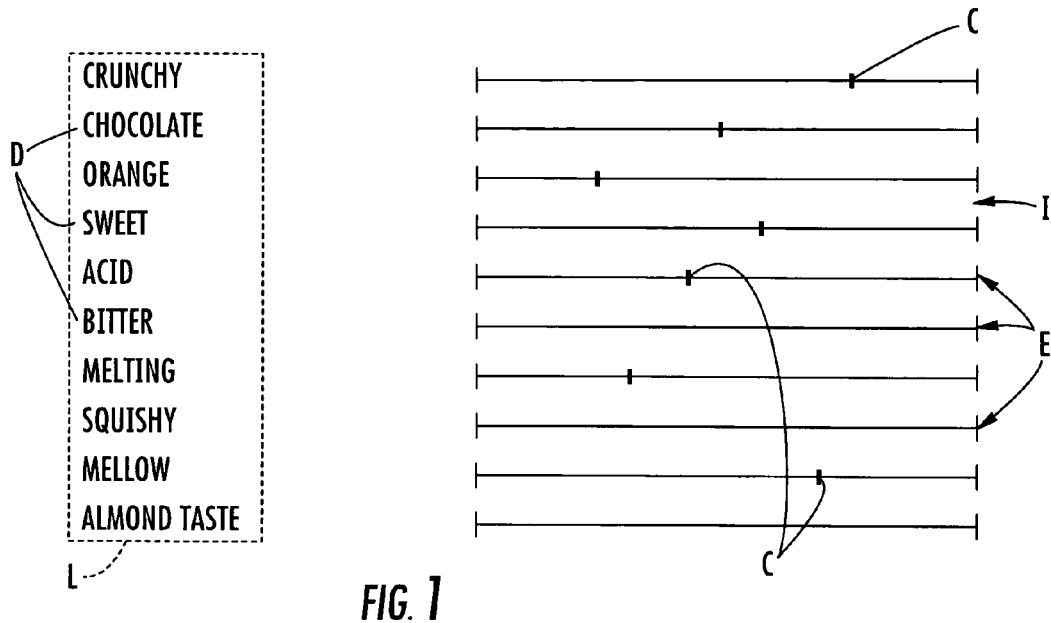
FIG. 1 shows a screen of a prior art measurement interface in which the descriptor input zones are in the form of a list.

The screen of FIG. 1 is an example of a prior art interface used for organoleptic analyses.

The work requested in this case of a panel of testers is to "mark" biscuits based on almond sponge, orange marmalade, and chocolate.

The interface I provides a list L of eleven descriptors D, each in register with a continuous intensity scale E provided with a slider C that can be moved by the testers.

The testers are requested to mark the intensity of each descriptor D for each biscuit by moving the slider C along the corresponding scale E.

The Applicant has found that testers perceive certain descriptors poorly because they mark the intensities of the descriptors in the order in which they are read, i.e. in this case: crunchy, chocolate, orange, etc. down to almond taste.

Figure 2:
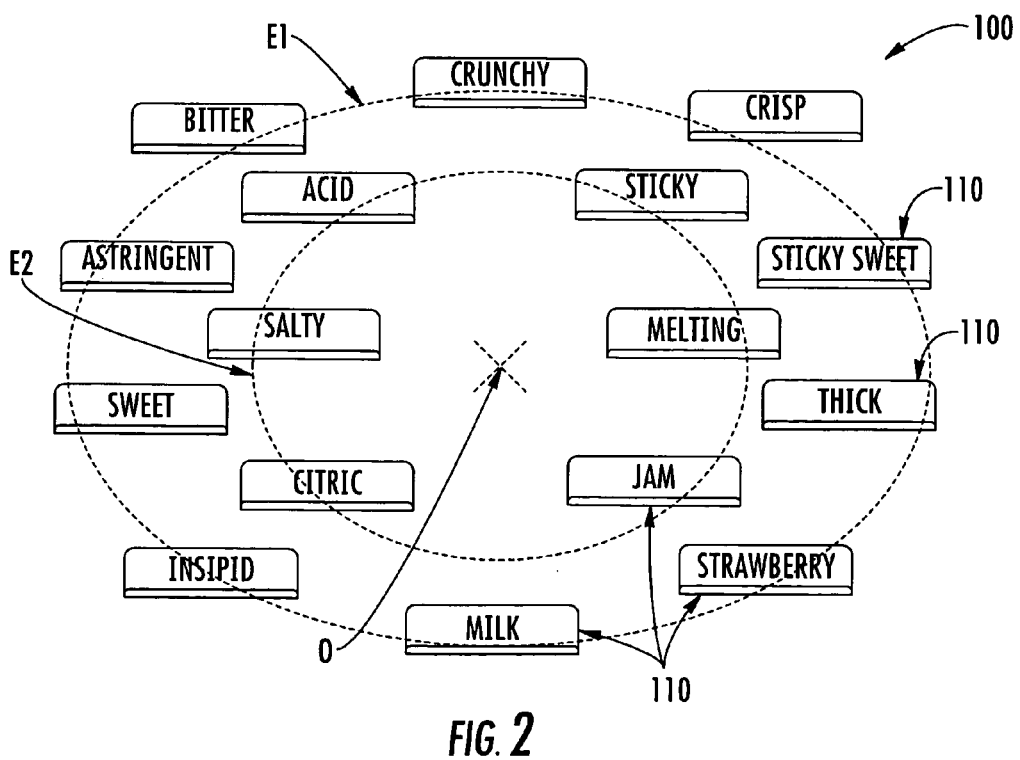
FIG. 2 shows a measurement interface of the invention presenting sixteen input zones distributed concentrically.
Figure 6:
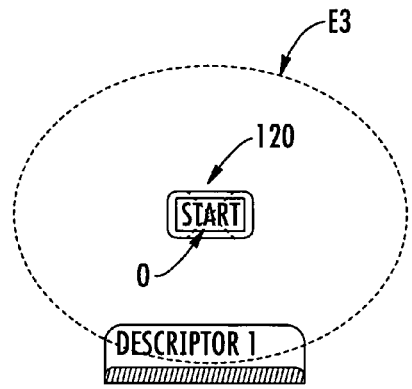
FIGS. 6 to 10 show a measurement interface of the invention presenting one to fifteen input zones distributed around an ellipse.
Figure 7:
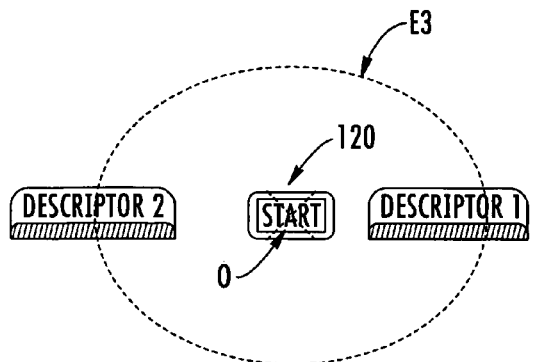
Figure 8:
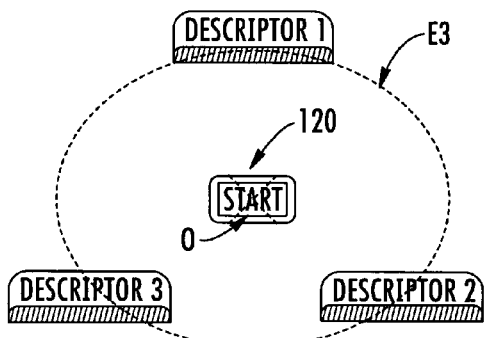
Figure 9:
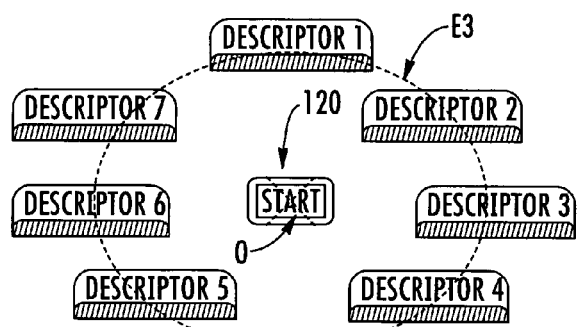
Figure 10:
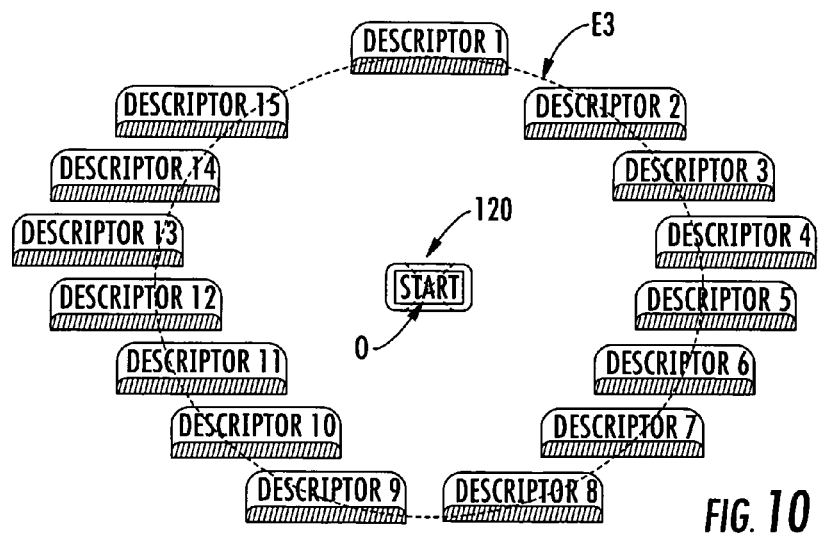
Figure 11:
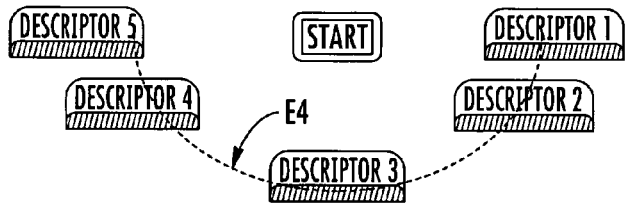
FIGS. 11 to 13 show an interface of the invention respectively presenting five, seven, and nine input zones in a bottom half-ellipse.
Figure 12:
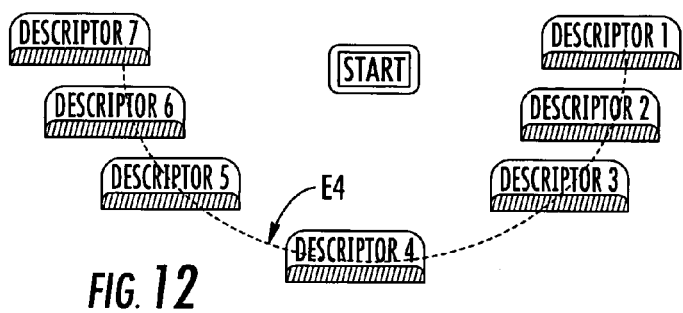
Figure 13:
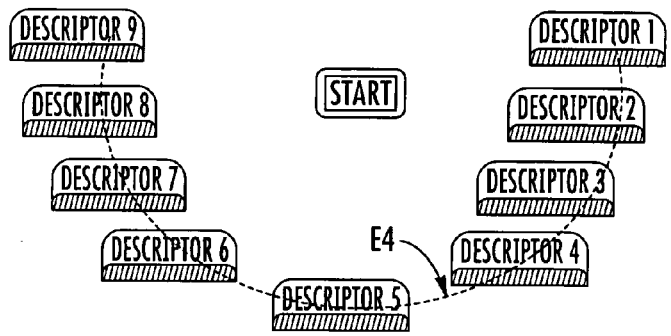

An embodiment of the invention is shown in FIG. 2 in the form of a screen constituting an interface 100 comprising a plurality of input zones 110, the number of zones corresponding to the number of descriptors selected for the analysis.

The input zones are constituted by buttons each comprising at least one sector carrying the wording of the descriptor.

The interface shown in FIG. 2 comprises sixteen input zones 110 corresponding to sixteen descriptors.

The input zones are distributed around two concentric ellipses E1 and E2 about the center O of the screen.

They are distributed in such a manner that the input zones 110 of the two ellipses are distributed in a staggered configuration.

When a button has only one input zone, it is merely activated by a tester selecting it, e.g. by means of a mouse click. A button of this type is shown in FIGS. 3a and 3b.

When the button is selected (FIG. 3b) it appears grayed out relative to the non-selected state (FIG. 3a) where the button appears in bright color.

Naturally, an alternative would be for the button to change color between the non-selected state and the selected state.

This on/off binary mode is used, for example, in order to mark the presence or the absence of a descriptor in the product (static marking method), or to mark the instant at which it appears or disappears while determining the organoleptic chronology of a product by a dynamic method (see definition below).

The buttons may comprise two or more sectors, one carrying the wording of the descriptor, and the other carrying means for marking the descriptor. Buttons of this type are shown in FIGS. 4, and 5a & 5b.

The button in FIG. 4 presents a second sector relating to a continuous range of values represented by continuously varying shading.

The tester thus moves the cursor to anywhere in the range as a function of the tester's assessment.

A variant is shown in FIGS. 5a and 5b.

The button of FIG. 5a has one sector carrying the wording of a descriptor, and another sector that is subdivided into a discrete number of values, specifically three values in this example.

When the tester selects the descriptor by clicking on the button, a slider appears and the tester places it on the value that is to be given (FIG. 5b).

An interface of the kind described above combined with buttons of the kinds shown in FIGS. 3 to 5 is particularly advantageous while performing organoleptic analyses by dynamic methods.

A dynamic method consists in measuring the sensations perceived over time while tasting a product. The ability to input over time enables the dynamic behavior of a product to be measured and shows up how the perceived sensations vary while tasting is taking place.

During a conventional sense profile session of static type, testers are required to give an intensity mark to each descriptor. That measurement method does not take account of the fact that the level of intensity perceived for a descriptor can vary over time while a product is being tasted.

A product can also be characterized by the dynamic behavior of the sensations perceived over time: a sensation or a flavor can appear in the mouth very late, or on the contrary it can disappear very early. Thus, it appears advantageous to integrate new methods of acquiring sense data to enable this time dimension to be taken into account.

Two products which present the same descriptors with the same intensities, but that appear at different moments, are not distinguished between by static methods, but they are by dynamic methods.

It is appropriate to use dynamic methods in particular:
  when the products are perceived to be different, in particular by consumers, even though their conventional profile does not enable this difference to be identified;
  as a complement to a conventional profile; and
  while evaluating complex descriptors (e.g. aromas) when the conventional profile is not sufficiently pertinent.

The use of an interface of the invention in combination with dynamic methods of organoleptic analysis is particularly advantageous compared with prior art interfaces.

An interface of the invention does not influence testers as to the order in which they mark descriptors, so firstly testers select descriptors in the real order in which they perceive them, and secondly they mark the descriptors accurately since they mark them at the same time as they select them, i.e. at the moment when they sense them. It is thus possible to give marks efficiently while minimizing the time or the duration between a sensation being perceived and being marked.

Three dynamic methods are considered more particularly:
  time-intensity (TI): consists in measuring variation in a single descriptor over time;
  super time-intensity (STI): consists in measuring variation in a plurality of descriptors over time; and
  sensation time dominance (STD): consists in measuring at each instant the descriptor that is most important for describing the product.

These methods apply to products for which dynamic variation in perception over time is perceived. For example, certain biscuits are products that it is advantageous to evaluate as a function of time for their texture and their aromas which vary over time.

The method of analysis of the invention is described below with reference to FIGS. 6 to 10 which show an interface for implementing the method in which the person in charge of the analysis has selected respectively two, three, seven and fifteen descriptors for determining the organoleptic characteristics of a biscuit X.

The person in charge has selected responses in a value range mode as shown in FIG. 4.

Thereafter the descriptors are supplied simultaneously to the panel of testers, on a single occasion, and for a determined duration, in a measurement interface that presents, for each descriptor, a respective input zone, the input zones being distributed uniformly around an ellipse E3 about the center O of the interface. Thereafter the responses are collected from each of the testers as a function of the selected response mode and then recorded and analyzed statistically.

The descriptors are shown on input zones 110 distributed uniformly around an ellipse E3 about the center O.

The interfaces shown are computer screens. The center O of the interface around which the input zones 110 are distributed can be empty, can present information, or else, as shown herein, can present an activatable "start" button 120.

The button 120 starts timing as soon as it is activated by a tester who thereby marks the beginning of tasting.

Such a button is dedicated more particularly for use in dynamic methods. Under such circumstances, the data collection step consists in selecting responses from each tester as a function of time.

The input zones are distributed uniformly around a center O so that a tester does not have any unconscious a priori preference for such and such a descriptor as a function of its position.

Thus, when a tester selects a descriptor, that selection is motivated by the perception of that descriptor without any contribution from the position of the descriptor in a particular order.

In another embodiment of the invention, the input zones are distributed uniformly around a half-ellipse. Preferably, and as shown in FIGS. 11 to 14, the input zones distributed around a half-ellipse E4 and E5 are situated, in use, below the foci of the half-ellipse.

When the distribution is around a complete conic (ellipse, circle), the number of descriptors proposed lies advantageously in the range two to sixteen, and is preferably ten for good legibility and so that the testers do not have any difficulty in finding the descriptors.

If the product may be characterized, a priori, by more than sixteen descriptors, the person in charge of experiments groups descriptors together in common categories (e.g. "dry cheese" and "sulfur cheese" can sometimes be grouped together under the descriptor "cheese").

While using the STD method, if a descriptor is mentioned for all of the products at the same moment, it is preferable to omit it. However, it is important to conserve a descriptor that is mentioned for two products only since that makes it possible to distinguish between them. A descriptor that is mentioned for all of the products but at different instants is also appropriate for retention in the list of descriptors.

When distribution is performed around a section of a conic (semicircle, half-ellipse, part of a hyperbola, part of a parabola), the number of descriptors proposed advantageously lies in the range two to eleven, and preferably in the range five to nine.

Figure 14:
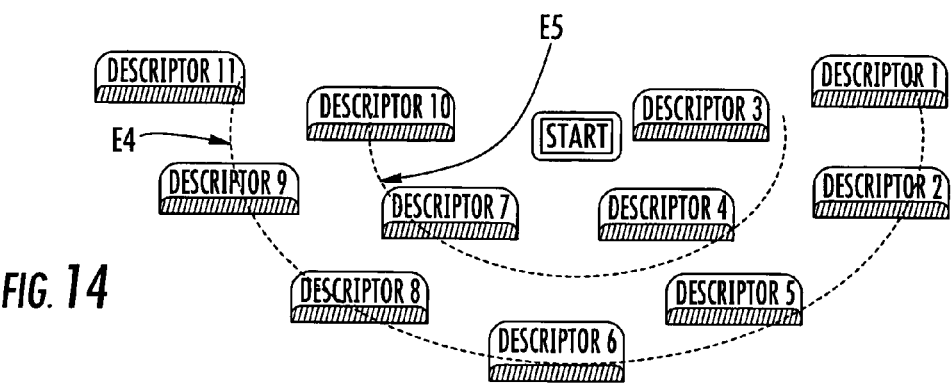
FIG. 14 shows an interface of the invention presenting eleven input zones distributed over two concentric half-ellipses.

FIG. 14 shows a distribution of eleven descriptors along two elliptical arcs.

Figure 15:
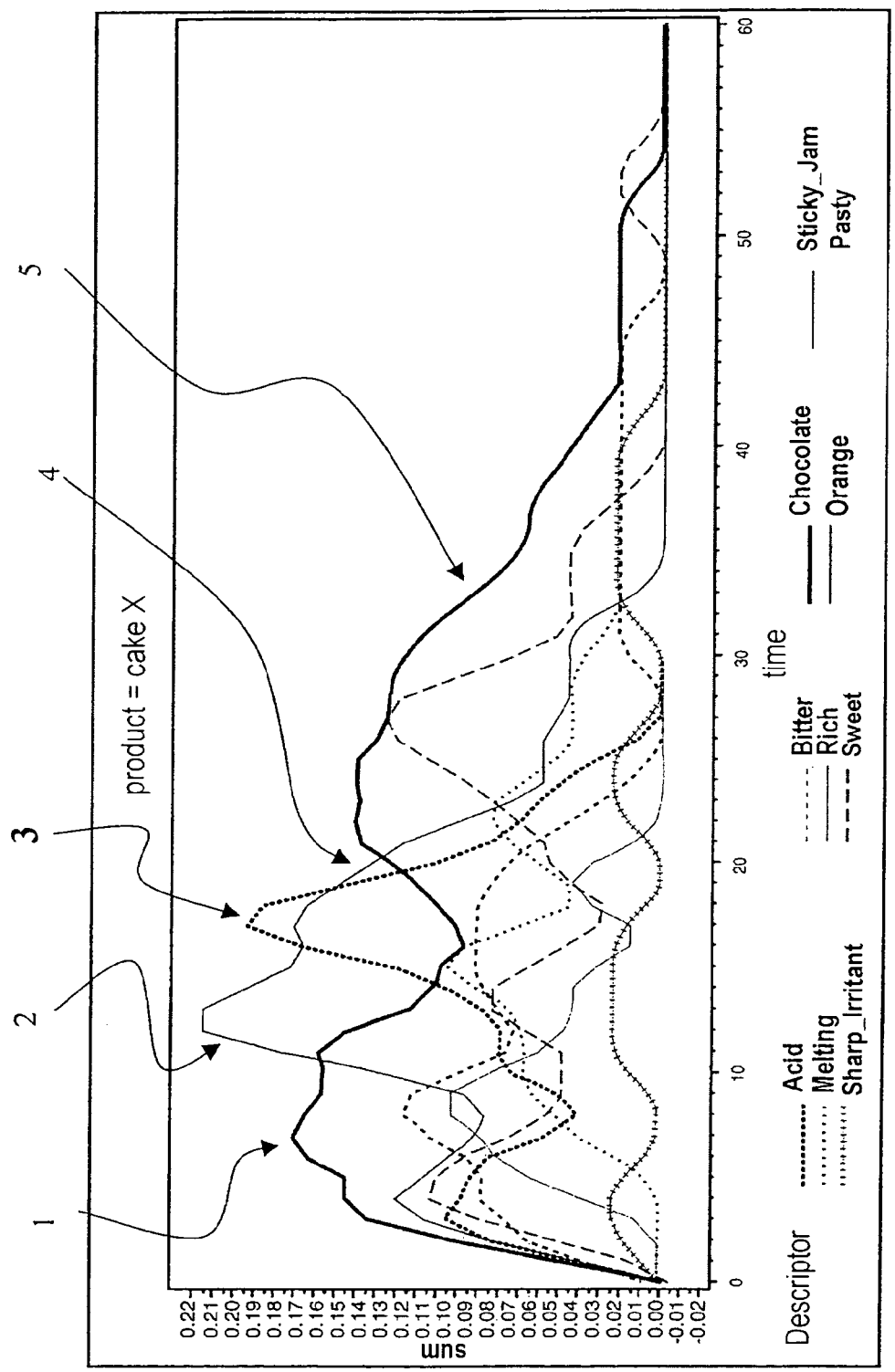
FIG. 15 is a graphical presentation of the results of an analysis performed in application of the method of the invention.

An example of a result of statistical analysis of an experiment performed by a panel of testers for a cake X is shown in FIG. 15.

This figure plots mention curves for all of the descriptors for a single product as a function of time. The range of the descriptor that is dominant as a function of time is given a successive reference 1 to 5. This display enables the mean sequence of descriptors to be visualized quickly.

The graphic of FIG. 15 shows that cake X is perceived as being successively "chocolate dominated" to begin with (zone 1), then "orange dominated" (zone 2), then "acid dominated" (zone 3), then "orange dominated" (zone 4), and again "chocolate dominated" (zone 5) as an after-taste.

When the interface of the invention is a computer screen, an electronic computer system is used for collecting, analyzing, storing, and displaying the results in automatic manner. Timing is then very accurate.

Thus, an example of an electronic system for implementing a measurement interface comprises a computer screen and a central processor unit (CPU) provided with digital and electronic means known to the person skilled in the art enabling the following actions to be undertaken:

initiating a memory when tasting begins at time to;

timing tasting for sixty seconds;

recording the time at which each tester's response occurs;

forming a multidimensional memory of cells each including a dimension corresponding to the descriptors and a dimension corresponding to the testers, and in which each cell corresponds to the combination of one descriptor and one tester;

storing in each cell one or more times at which the descriptor occurs for each tester (FIG. 15 shows that the chocolate descriptor was perceived in characteristic manner by the testers at times 3 seconds (s) to 10 s, at times 21 s to 26 s, and then at times 29 s to 43 s), where an occurrence time can be null if the tester does not select the descriptor during tasting;

performing statistical processing on the cells in application of the STD method selected by the operator;

storing the results of said processing in a memory; and providing a record of the results displaying the following organoleptic characteristics "acid", "melting", "sharp irritant", "bitter", "rich", "sweet", "chocolate", "orange", "sticky-jam", and "pasty" for the cake X as a function of time.

The system also stores in each cell an intensity for the descriptor for each tester, where a descriptor intensity is a continuous value in a range of values.

Such a system is advantageous when the experiment consists in testing only one product at a time.

An improvement can be provided to this first display. It consists in displaying the curves by centering them on the means of other products.

Thus, on per product curves, for the descriptors k at an instant t, the following is plotted:

$$f(k)-f$$

where $f(k)$ is the frequency of the descriptor k, and f is the mean frequency of the descriptor k over all of the products at instant t.

Figure 16:
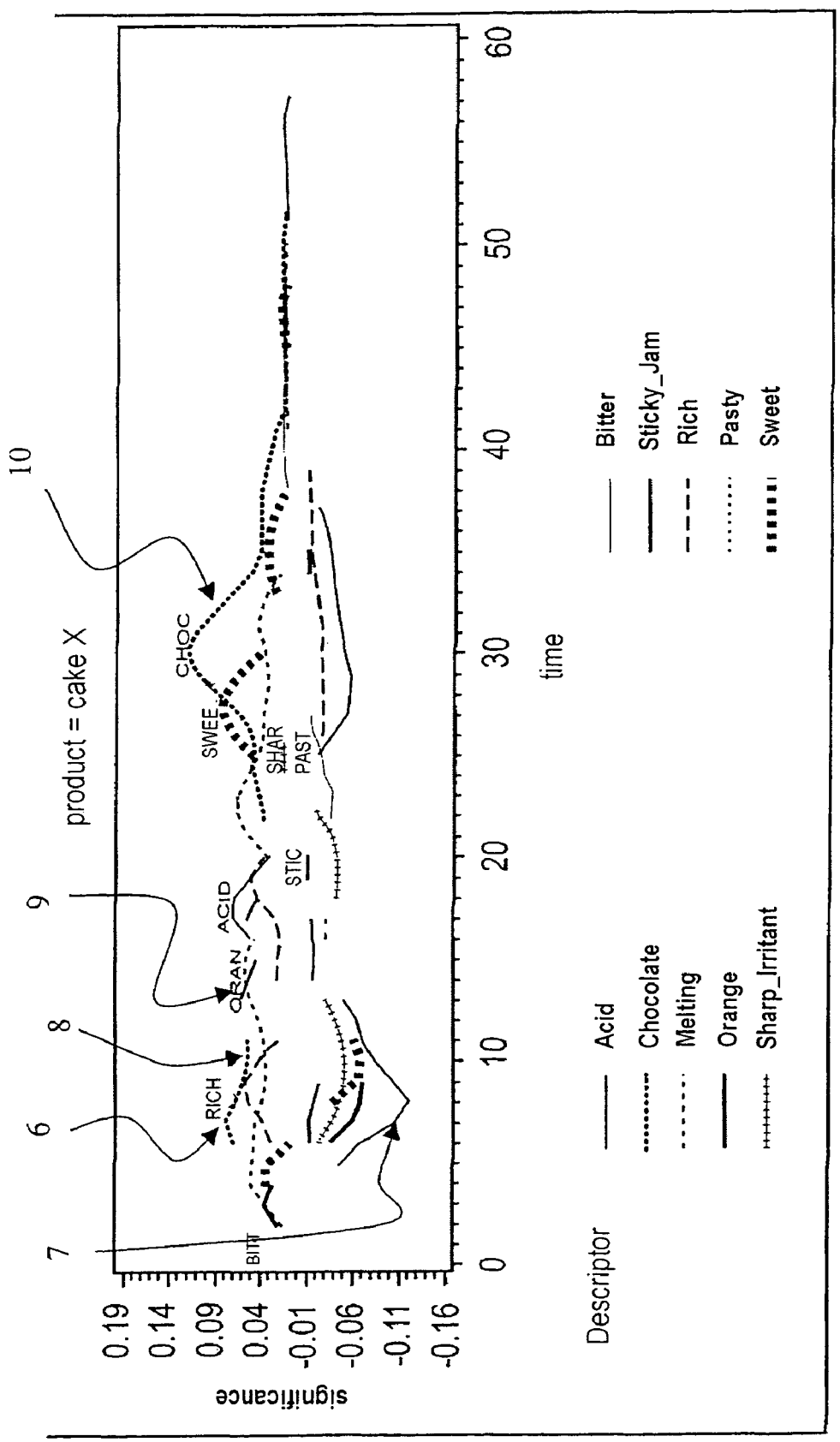
FIG. 16 is a graphical presentation of the results of an analysis of a cake, the results being centered about the mean.

This graphic display presents the advantage of making it easier to compare a plurality of products. When the experiment is being performed on one particular product, the record shown in FIG. 16 shows the mention curves for all of the descriptors of that one product as a function of time. The ranges of the descriptors that are dominant as a function of time are given successive references 6 to 10.

This display shows quickly the mean sequence of descriptors characterizing the product in a manner that is meaningful compared with the other products.

This display gives the "organoleptic spectrum" of a product and makes it possible to achieve an effective comparison with other products in comparison with records of the same type made for the other products.

Reading the graphic of FIG. 16 shows that cake X is perceived initially as being chocolate 6, then not very acid 7, then chocolate 8, then orange 9, and then very chocolate 10 as an after-taste compared with the other products.

Figure 17:
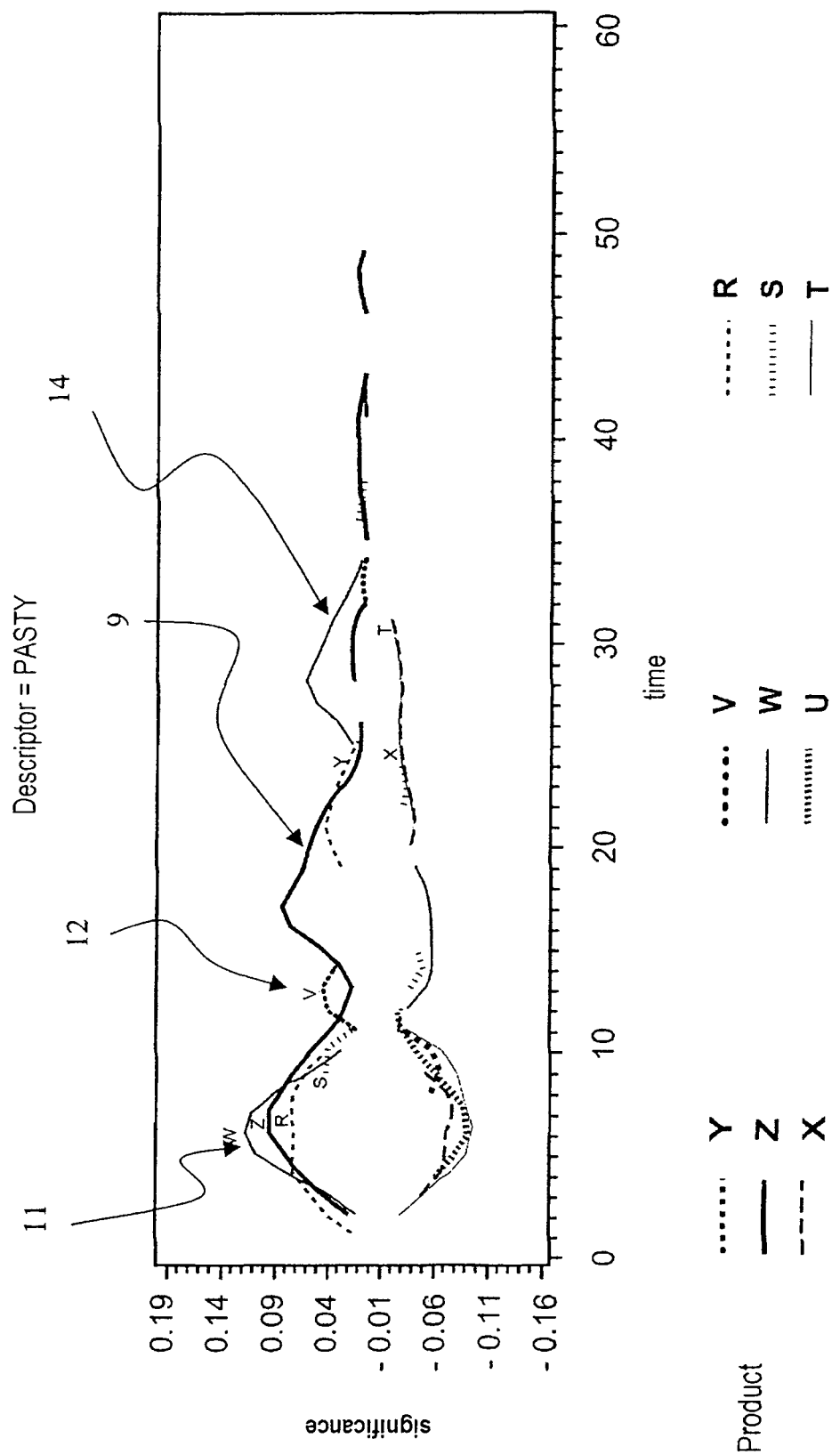
FIG. 17 is a graphical presentation of results of an analysis in application of the same descriptor on a plurality of cakes of different brands and centered relative to the mean.

FIG. 17 plots mention curves relating to a single descriptor for all of the products as a function of time. The ranges of the values that are dominant as a function of time are referenced 11 to 14.

This display enables products to be distinguished by the perceived sequencing of the descriptors under consideration.

When the experiment seeks to analyze a plurality of products in order to compare them, a variant of the above-described electronic system consists in initializing the memory, in storing the numbers and the identities of the products to be tested, and while forming the multidimensional memory, forming a multidimensional memory of cells having one dimension corresponding to the descriptors, one dimension corresponding to the testers, and one dimension corresponding to the tested products, each cell corresponding to the combination of one descriptor, one tester, and one product. In each cell, the system also stores at least one descriptor intensity for each tester, where a descriptor intensity is a continuous value in a range of values.

In order to improve the pertinence of the results, the tests for one or more products can be repeated several times for a given tester and the same descriptors. Each test is then referred to as a "repeat". Thus, a variant of the above-described electronic systems consists in initializing the memory, in storing the number and the identities of the repeats, and during the step of forming the multidimensional memory, of forming a multidimensional memory having cells with an additional dimension corresponding to the repeats.

For example, when tests are carried out on a plurality of products, and with a plurality of repeats, each cell corresponds to the combination of one descriptor, one tester, one repeat, and one product.

Reading the graphic of FIG. 17 shows that product W is initially perceived as being the pastiest 11, after which it is V 12, Z 13, and W 14 that are again perceived as being very pasty compared with the other products in terms of persistence.

In order to improve the pertinence of the results, while implementing the method it is possible during the step of analyzing the responses to perform the following operations:

filtering out of data that is not representative as detected while analyzing the responses; and processing of the data using the statistical method for characterizing the products.

To do this, prior to the step of statistical processing, the electronic system determines and initializes cells that contain results that are not representative compared with the set of cells for the descriptors selected by an operator.

This type of filtering is known to the person skilled in the art.

Such representations constitute the results of analyses of industrial food products, of cosmetics, and/or of hygiene products.

They enable the person skilled in the art, on interpreting them, to understand how the manufactured product is perceived by the final user. It is then possible to modify the composition and/or to modify concentrations in order to improve the product from an organoleptic point of view.

The pertinence and the accuracy of organoleptic analyses are of very great importance for manufacturing and selling such products, with the interface making it possible by its very structure to improve such analyses, and consequently to improve the products.

By means of the method, the interface, and the electronic system of the invention, it is possible to analyze numerous products: cosmetics or hygiene products (analyzing their fatty or other feel, their capacity to be absorbed by the skin, their fragrance, their texture, etc. . . . ).

The present invention is not limited to the embodiments and implementations described or shown.

In other embodiments of the invention:

the interface is a touch-sensitive computer screen; the tester no longer uses a mouse but taps directly on the screen;

the interface is a sheet of paper on which input zones are printed and distributed in uniform manner along at least one section of at least one conic about a center of the interface; each input zone comprises a sector labeled by a descriptor, a marking sector (e.g. for marking intensity), and optionally for use in a dynamic method, at least one sector where testers mark an identifier giving the order in which the descriptor arises (measured time or order number); when using order numbers, it is the sequence which is analyzed; naturally the same descriptor may appear several times over, e.g. both in a second position and in a sixth position; in which case the sensor will mark the numbers 2 and 6 in the sector.

What is claimed is:

1. A method of analyzing a product having organoleptic characteristics in order to characterize, distinguish, and/or modify the product by analyzing the responses of a panel of testers to certain descriptors, the method comprising the steps of:

a) selecting descriptors that are pertinent a priori for determining the organoleptic characteristics of the product;

b) selecting a response mode selected from the group consisting of an on/off binary mode, a continuous mode over a range of values, and a discrete mode over a range of values;

c) providing all of the descriptors simultaneously to the panel of testers for a determined duration in a measurement interface presenting a center and an input zone for each descriptor, the input zones being distributed uniformly over at least a section of at least one conic about the center of the interface in a relative arrangement, locations of the input zones being determined without regard to any particular sequence or order of appearance so that the testers are not influenced by the order in which the descriptors appear;

d) collecting the responses from each tester as a function of the selected response mode, said responses being without influence by the order in which the descriptors appear;

e) recording the responses;

f) determining a result set of organoleptic characteristics describing the product by implementing a computer configured to apply at least one statistical method to the responses and g) providing a record of the result set of organoleptic characteristics in a user readable format.

2. A method according to claim 1, in which the descriptors are distributed in a different manner on the interface of each member of the panel of testers.

3. A method according to claim 1, in which step d) comprises collecting the responses from each tester as a function of time.

4. A method according to claim 1, in which the statistical method is a time independent method.

5. A method according to claim 1, in which the statistical method is a time dependent dynamic method.

6. A method according to claim 5, in which the dynamic method is selected from the group consisting of:

a time-intensity method, wherein variation in a single descriptor over time is measured;

a super time-intensity method, wherein variation in a plurality of descriptors over time is simultaneously measured; and a sensation time dominance method, wherein, at each instant, the descriptor that is the most important for describing the product at that instant is measured.

7. A method according to claim 1, in which step f) comprises filtering out data that is not representative, as detected while analyzing the responses; and processing the representative data using the statistical method.

8. A method of analyzing a product having organoleptic characteristics in order to characterize, distinguish, and/or modify the product by analyzing the responses of a panel of testers to certain descriptors, the method comprising the steps of:

a) selecting descriptors that are pertinent a priori for determining the organoleptic characteristics of the product;

b) selecting a response mode selected from the group consisting of an on/off binary mode, a continuous mode over a range of values, and a discrete mode over a range of values;

c) providing all of the descriptors simultaneously to the panel of testers for a determined duration in a measurement interface presenting a center and an input zone for each descriptor, the input zones being distributed uniformly, without order indication and in the same reading orientation over at least a section of at least one conic about the center of the interface, locations of the input zones being determined without regard to any particular sequence or order so that the testers are not influenced by the order in which the descriptors appear;

d) collecting the responses from each tester as a function of the selected response mode, said responses being without influence by the order in which the descriptors appear;

e) recording the responses;

f) determining a result set of organoleptic characteristics describing the product by implementing a computer configured to apply at least one statistical method to the responses, and g) providing a record of the result set of organoleptic characteristics in a user readable format.

9. A method according to claim 8, in which the descriptors are distributed in a different manner on the interface of each member of the panel of testers.

10. A method according to claim 8, in which step d) comprises collecting the responses from each tester as a function of time.

11. A method according to claim 8, in which the statistical method is a time independent method.

12. A method according to claim 8, in which the statistical method is a time dependent dynamic method.

13. A method according to claim 12, in which the dynamic method is selected from the group consisting of:

a time-intensity method, wherein variation in a single descriptor over time is measured;

a super time-intensity method, wherein variation in a plurality of descriptors over time is simultaneously measured; and a sensation time dominance method, wherein, at each instant, the descriptor that is the most important for describing the product at that instant is measured.

14. A method according to claim 8, in which step f) comprises: filtering out data that is not representative, as detected while analyzing the responses; and processing the representative data using the statistical method.

15. A method according to claim 1 wherein step g) comprises providing a graphic display of the result set of organoleptic characteristics.

16. A method according to claim 8 wherein step g) comprises providing a graphic display of the result set of organoleptic characteristics as a function of time.

* * * * *

UNITED STATES PATENT AND TRADEMARK OFFICE
CERTIFICATE OF CORRECTION

PATENT NO. : 7,577,530 B2
APPLICATION NO. : 10/951235
DATED : August 18, 2009
INVENTOR(S) : Anne Vignalou-Marche It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 568 days.

Signed and Sealed this

Seventh Day of September, 2010

David J. Kappos
*Director of the United States Patent and Trademark Office*